United States Patent [19]

Izraelev

[11] Patent Number: 5,938,412
[45] Date of Patent: *Aug. 17, 1999

[54] BLOOD PUMP HAVING ROTOR WITH INTERNAL BORE FOR FLUID FLOW

[75] Inventor: Valentin M. Izraelev, Eden Prairie, Minn.

[73] Assignee: Advanced Bionics, Inc., Eden Prairie, Minn.

[ * ] Notice: This patent is subject to a terminal disclaimer.

[21] Appl. No.: 08/886,188

[22] Filed: Jul. 1, 1997

Related U.S. Application Data

[63] Continuation-in-part of application No. 08/456,503, Jun. 1, 1995, Pat. No. 5,685,700.

[51] Int. Cl.$^6$ .................................................. F04B 35/04
[52] U.S. Cl. ................. 417/423.7; 417/423.14; 417/424.1; 417/355; 415/206; 415/900
[58] Field of Search ..................... 415/203, 206, 415/900; 600/16; 604/4, 131, 151; 417/420, 423.14, 423.7, 424.1, 356, 357; 623/3; 416/186 R, 189

[56] References Cited

U.S. PATENT DOCUMENTS

| 2,319,730 | 5/1943 | Garraway . |
| 3,433,163 | 3/1969 | Sheets et al. . |
| 3,647,324 | 3/1972 | Rafferty et al. ......................... 417/420 |

(List continued on next page.)

FOREIGN PATENT DOCUMENTS

| 2342767 | 3/1975 | Germany . |
| 3130974 A1 | 2/1983 | Germany . |
| 1359007 | 4/1974 | United Kingdom . |

OTHER PUBLICATIONS

Olsen et al., "Blood Pump with a Magnetically Suspended Impeller", *Trans. Am. Soc. Artif. Intern. Organs*, vol. XXXI, 1985, pp. 395–401.

Bramm et al., "The Sealless and Bearingless Rotor Blood Pump System: Adaptation..Thermal Heat UP" Assisted Circulation 3, F. Unger (Ed.), Springer–Verlag Berlin Heidelberg, 1989, pp. 215–224.

Ohara et al., "The Next Generation Baylor C–Gyro Pump: Anthithrombogenic 'Free Impeller' Design for Long–Term Centrifugal VAD", *Artif. Organs*, vol. 18, #3, 1994, pp. 238–243.

Treichler et al., "A Fluid Dynamic Analysis of a Rotary Blood Pump for Design Improvement", *Artif. Organs*, vol. 17, No. 9, 1993, pp. 797–808.

Nishida et al., "Development of the Terumo Capiox Centrifugal Pump and Its Clinical . . . Roller Pump", *Artif. Organs*, vol. 17, No. 4, 1993, pp. 323–327.

Araki et al., "A Flow Visualization Study of Centrifugal Blood Pumps Developed for Long–Term Usage", *Artif. Organs*, vol. 17, No. 5, 1993, pp. 307–312.

Bramm et al., "Reduction of Coagulation and Hemolysis . . . for Long–Term Application", pp. 175–179.

(List continued on next page.)

*Primary Examiner*—Charles G. Freay
*Attorney, Agent, or Firm*—Haugen Law Firm PLLP

[57] ABSTRACT

A pump for transferring fragile and aggressive fluids such as human blood and comprising a pumping chamber along with a fluid inlet port disposed on the chamber, and one or more outlet ports arranged transversely and medially of the inlet ports. A shrouded rotor is positioned within the pumping chamber having a core of dual-conical configuration converging toward opposed polar end regions and with an axis of rotation extending between the polar regions. The shrouded rotor includes magnets which are arranged at radially spaced locations and with a magnetic drive positioned to deliver rotational driving energy to the rotor. The sole support for the rotor are the hydrodynamic forces acting upon the rotor during its operation, with the rotor body having a relative density of between 10% and 90% of the relative density of the fluid being pumped.

12 Claims, 3 Drawing Sheets

U.S. PATENT DOCUMENTS

| | | |
|---|---|---|
| 3,890,019 | 6/1975 | Boden et al. . |
| 3,957,389 | 5/1976 | Rafferty et al. . |
| 3,970,408 | 7/1976 | Rafferty et al. . |
| 4,036,565 | 7/1977 | Becker . |
| 4,057,369 | 11/1977 | Isenberg et al. . |
| 4,507,048 | 3/1985 | Belenger et al. .......................... 415/90 |
| 4,688,998 | 8/1987 | Olsen et al. . |
| 4,779,614 | 10/1988 | Moise . |
| 4,944,748 | 7/1990 | Bramm et al. . |
| 4,994,078 | 2/1991 | Jarvik . |
| 4,995,857 | 2/1991 | Arnold . |
| 5,049,134 | 9/1991 | Golding et al. . |
| 5,055,005 | 10/1991 | Kletschka . |
| 5,078,741 | 1/1992 | Bramm et al. . |
| 5,112,200 | 5/1992 | Isaacson et al. . |
| 5,158,440 | 10/1992 | Cooper et al. . |
| 5,195,877 | 3/1993 | Kletschka . |
| 5,205,721 | 4/1993 | Isaacson . |
| 5,211,546 | 5/1993 | Isaacson et al. . |
| 5,326,344 | 7/1994 | Bramm et al. . |
| 5,385,581 | 1/1995 | Bramm et al. . |
| 5,443,503 | 8/1995 | Yamane . |
| 5,470,208 | 11/1995 | Kletschka . |

OTHER PUBLICATIONS

Sasaki et al., "A Compact Centrifugal Pump for Cardiopulmonary Bypass", *Artif. Organs*, vol. 16, No. 6, 1992, pp. 592–598.

Ohara et al., "An Ultimate Compact, Seal–less Centrifugal Ventricular Assist Device: Baylor C–Gyro Pump", *Artif. Organs*, vol. 18, No. 1, 1994, pp. 17–24.

Makinouchi et al, "Internal Hydraulic Loss in a Seal–less Centrifugal Gyro Pump", *Artif. Organs*, vol. 18, No. 1, 1994, pp. 25–31.

Kijima, et al, "The Margin of Safety in the Use of a Straight Path Centrifugal Blood Pump", *Artif. Organs*, vol. 18, No. 9, 1994, pp. 680–686.

Araki et al, "A Flow Visualization Study of the NCVC Centrifugal Blood Pump", *Artif. Organs*, vol. 18, No. 9, 1994, pp. 669–672.

Kabei et al, "Concept Designs of Nonrotating–type Centrifugal Blood Pump..Disc–type Centrifugal Pump", *Artif. Organs*, vol. 18, No. 9, 1994, pp. 657–663.

Schima et al., "The Vienna Implantable Centrifugal Blood Pump", *Artif. Organs*, vol. 18, #7, 1994, pp. 500–505.

Ohara et al., "Development and Evaluation of Antithrombogenic Centrifugal Pump: The Baylor..Inlet Port Model", *Artif. Organs*, vol. 18, No. 9, 1994, pp. 673–679.

Taguchi, et al., "A Miniaturized Centrifugal Pump for Assist Circulation", *Artif. Organs*, vol. 18, No. 9, 1994, pp. 664–668.

Akamatsu et al., "Centrifugal Blood Pump with a Magnetically Suspended Impeller", *Artif. Organs*, vol. 16, No. 3, 1993, pp. 305–308.

Miller et al., "Evaluation of Multiple Disk Centrifugal Pump as an Artificial Ventricle", *Artif. Organs*, vol. 17, No. 7, 1993, pp. 590–592.

Ohara et al., "Baylor Gyro Pump: A Completely Seal–less-..Long–Term Circulatory Support", *Artif. Organs*, vol. 17, No. 7, 1993, pp. 599–604.

Schima et al., "In Vitro Investigation of Thromboenesis in Rotary Blood Pumps", *Artif. Organs*, vol. 17, No. 7, 1993, pp. 605–608.

Kijima et al., "A Straight Path Centrifugal Blood Pump Concept in the Capiox Centrifugal Pump", *Artif. Organs*, vol. 17, No. 7, 1993, pp. 593–598.

Naito et al., "Developments of the Baylor–Nikkiso Centrifugal Pump with . . . Circulatory Support", *Artif. Organs*, vol. 17, No. 7, 1993, pp. 614–618.

Damm et al., "In Vitro Performance of the Baylor/NASA Axial Flow Pump", *Artif. Organs*, vol. 17, #7, 1993, pp. 609–613.

Yada et al., "Clinical Experience Using the Bio–Pump for Extracorporeal Circulation during Open–Heart Surgery", *Artif. Organs*, vol. 17, No. 7, 1993, pp. 619–624.

Nishida et al., "Clinical Experience of Assisted Circulation with . . . Women's Medical College", *Artif. Organs* vol. 17, No. 7, 1993, pp. 625–629.

Curtis et al., "Clinical Experience with the Sarns Centrifugal Pump", *Artif. Organs*, vol. 17, No. 7, 1993 pp. 630–633.

Affeld et al., "A New Electrohydraulic Energy Concerter for a Left Ventricular Assist Device", *Artif. Organs*, vol. 18, No. 7, 1994, pp. 479–483.

Curtis et al., "Frequency of Seal Disruption with the Sarns Centrifugal Pump in Postcardiotomy Circulatory Assist", *Artif. Organs*, vol. 18, No. 3, 1994, pp. 235–237.

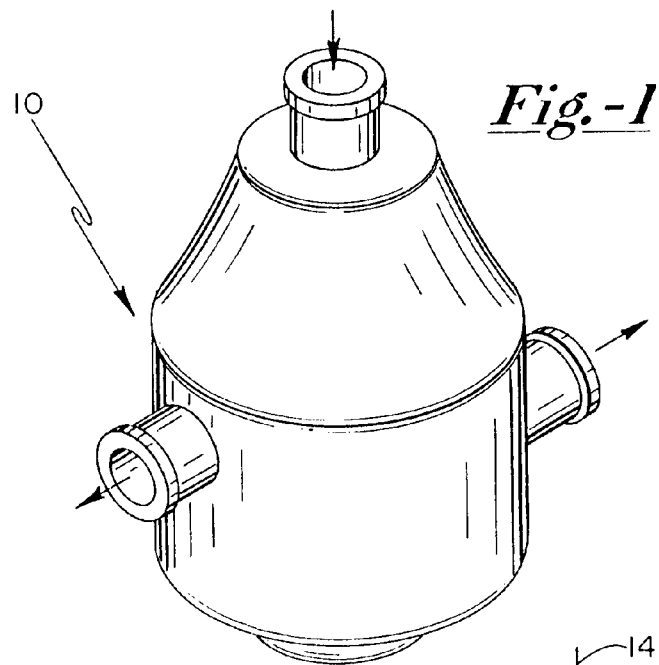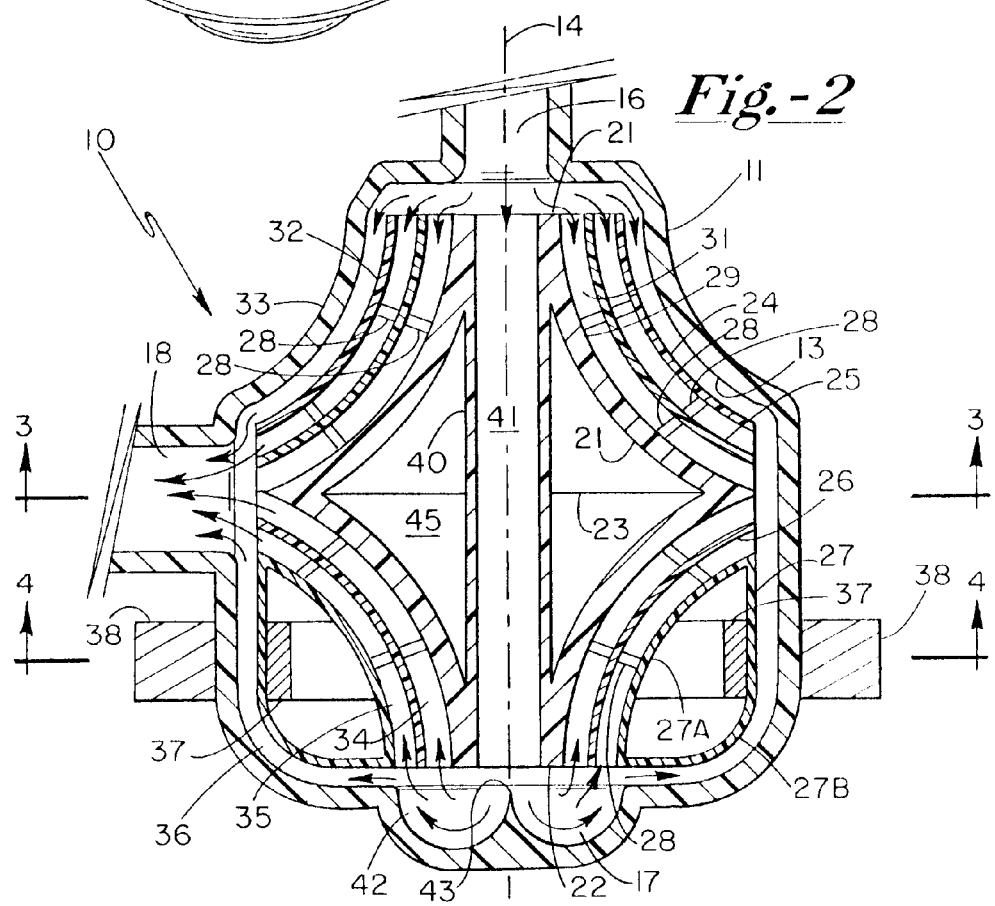

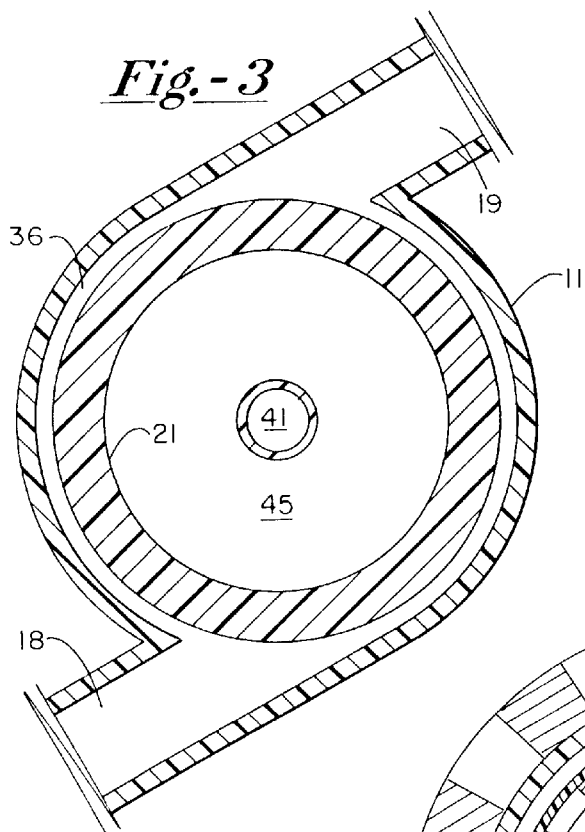
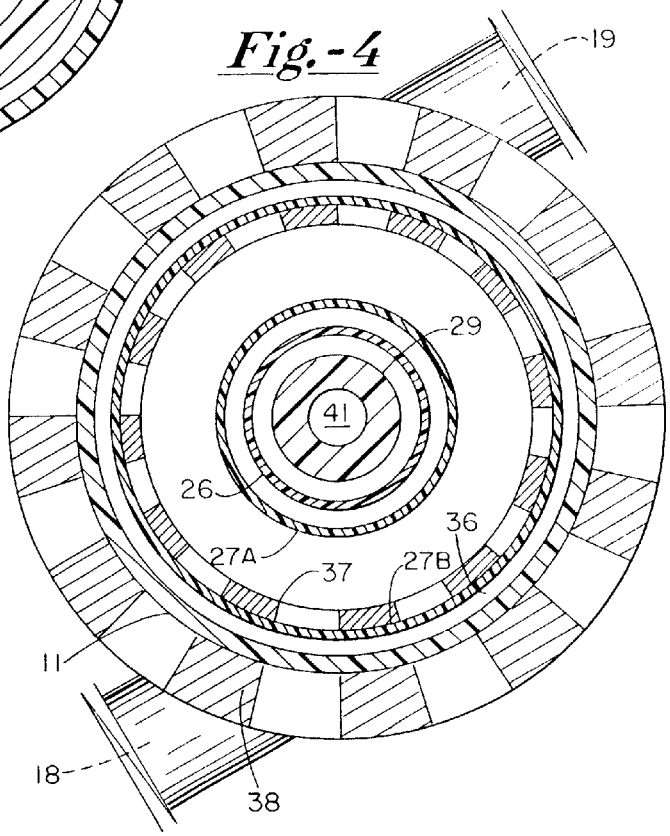

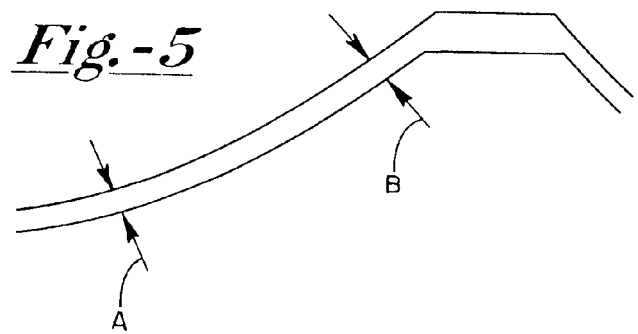
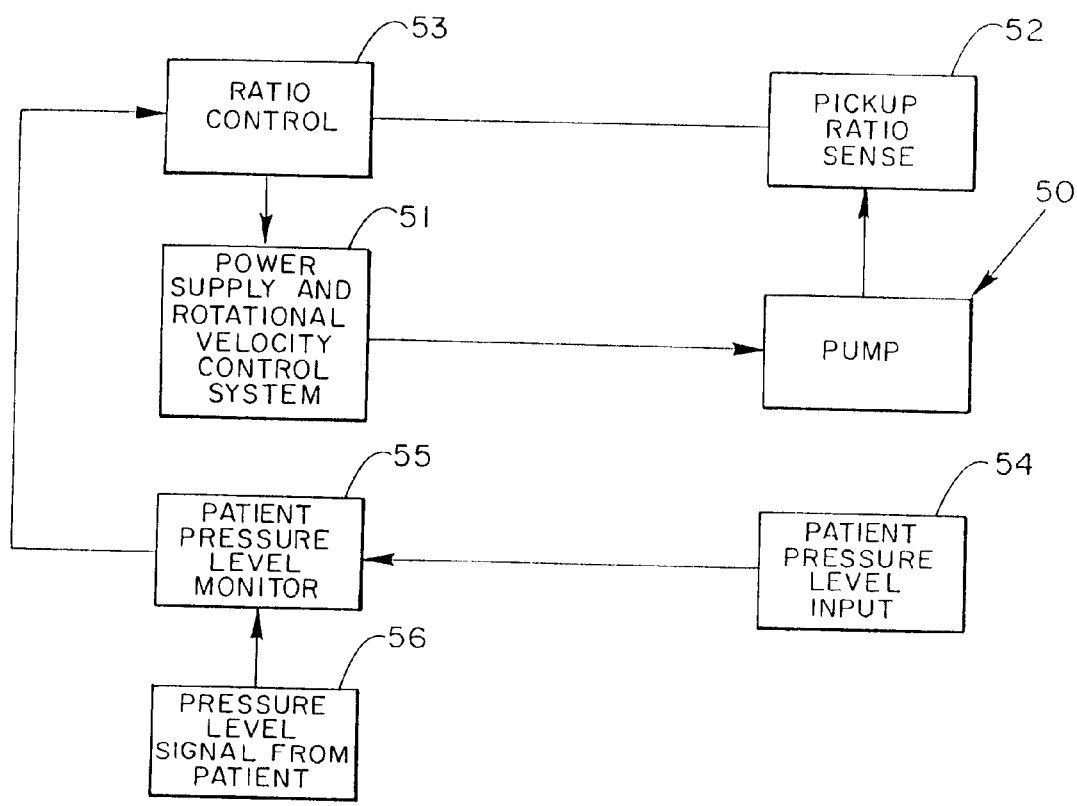

BLOOD PUMP HAVING ROTOR WITH INTERNAL BORE FOR FLUID FLOW

CROSS-REFERENCE TO RELATED APPLICATION

The present application is a continuation-in-part of my copending application Ser. No. 08/456,503, filed Jun. 1, 1995, entitled "BLOOD PUMP", now U.S. Pat. No. 5,685,700, issued Nov. 11, 1997 and assigned to the same assignee as the present invention.

BACKGROUND OF THE INVENTION

The present invention relates generally to an improved rotor design for a pump for transferring fragile or aggressive fluids. Examples of fragile fluids include human or animal blood, neither of which can tolerate exposure to unusual impact and/or sheer forces. Aggressive fluids include corrosive or poisonous fluids, as well as fluids which cannot tolerate contamination, or which otherwise may destroy seals and/or bearings to reduce the lifetime and/or longevity of the pump structure. Poisonous fluids, for example, are extremely dangerous if a leak develops. More particularly, the present invention relates to a rotor design for a pump which is bearing and seal-free and wherein the rotor is dynamically balanced by a combination of hydrodynamic and buoyant forces. The pump of the present invention is particularly adapted for transferring human blood and is capable of creating a flow of such liquids without damaging and/or otherwise adversely affecting the quality of the material being pumped. The rotor employed in the pump of the present invention is rotated electromagnetically by means of an electromagnetic drive system operating in conjunction with an array of permanent magnets disposed on the rotor in a brushless motor configuration. Alternatively, a permanent magnet-to-permanent magnet coupling may be employed. As such, the arrangement of the present invention is capable of achieving relative rotation while at the same time being bearing and seal-free.

In the past, pumps and pumping systems have been designed utilizing rotors which have been characterized as being bearing and seal-free. Such systems typically employ magnetic levitation means which is in effect an actual form of bearing, much the same as sleeve bearings, ball bearings, or other friction-inducing bearings. Such arrangements using magnetic bearings, while being operational and functional, may be rendered complex and accordingly require significant number of additional components including magnetic devices, position sensors, and rapid-response magnetic drive means. A number of such patents have been granted in the past, including those to Olsen et al. U.S. Pat. Nos. 4,688,998 and 5,195,877. The apparatus of the present invention, by contrast, is fully bearing and seal-free, and is provided with a rotor having a central internal bore to accommodate fluid flow input, as well as externally-positioned annular channels for accommodating flow through the pump structure. The rotor of the present invention is further designed so as to function with dynamic balance being achieved through a combination of hydrodynamic and buoyant forces.

Among the disadvantages inherent in pumps utilizing friction-reducing bearings include local heat generation such as may occur from the use of ball bearings, friction bearings, sleeve bearings, and the like. Low flow and high pressure may result in local areas due to the use of such structures. In addition, with all such bearing-equipped pumps, a high spring constant is provided wherein a small displacement of the rotor (or impeller) introduces very high forces which can damage or effectively destroy bearings. In addition, different forces are introduced in the structure whenever variations in axial positions occur.

In the present structure, the pump is bearing and seal-free, with the structure including a rotor having an internal bore for accommodating inlet fluid, and is further provided with a series of external shrouds providing multiple annular flow channels, with this design allowing for relatively high displacement without the creation of large forces otherwise required to hold a rotor in its predetermined position. The internal bore formed within the rotor is arranged coaxially with the rotor and thus fluid flow is readily accomplished therewithin. In addition, the rotor seeks and finds an equilibrium position which in certain situations can be off-set from the housing axis (in either the rotational or transverse axes) which typically occurs when the rotational axis of the pump is altered. Rotational movement of the pump housing will be manifested in displacement of the rotational or vertical axis of the rotor. The present arrangement has been found to eliminate the need for a highly precise axis in design, fabrication and operation. The lack of a positionally fixed rotational axis reduces the introduction of large forces which otherwise would be created when the axis of the rotor is shifted away from its normal centrally disposed position.

In the arrangement of the present invention, the pump includes a pumping chamber with a central axis, and with a rotor body being disposed within the chamber for bearing and seal-free rotation therewithin. The rotor has a core with a double or dual-conical configuration converging toward opposed polar regions, and with the axis of rotation extending between these polar regions. A fluid inlet port is arranged in the pumping chamber with a bore coaxially with the axis of rotation of the rotor in order to provide for inlet flow to opposed ends of the rotor. In this arrangement, the housing inlet flow is divided into two approximately equal flow portions, with the first flow portion entering the rotor at the end adjacent the housing inlet or the external inlet, and the second flow portion being drawn through the bore to the housing end opposite to the external inlet where the second flow portion makes a smooth reversal of direction and enters the rotor at the opposed end. Accordingly, one portion of the flow of fluid is transported or transferred to the portion of the rotor which is in opposed polar relationship to the housing inlet port, in other words, the external inlet. Except for those occasions when the rotor is displaced, it is normally arranged in coaxial relationship with both the pumping chamber and the fluid inlet ports. The outlet port or ports are arranged generally medially of the chamber, midway between the ends of the rotor and typically are positioned tangentially of the medial portion of the rotor and the pumping chamber. In those situations where the axis of rotation of the rotor is arranged vertically, the modified dual-conical configuration is such that flow through the bore of the rotor proceeds downwardly on the bore portion, and downwardly or upwardly on the portions external to the dual-cone shaped core.

The present rotor provides for an internal transfer of fluids between the oppositely disposed fluid inlet areas with the rotor bore forming a fluid transfer line which introduces the fluids to the rotor at opposite ends of the housing. The bore provides communication between opposite ends of the rotor, thereby permitting transfer of fluids internally of the structure, with all of the fluid being initially introduced into one polar region of the housing. The fluid is thereafter transferred internally to the oppositely disposed polar region.

The pump shown in the drawings is in operational mode with the rotor spinning about its axis of rotation and with all forces acting on the rotor balanced. In the stationary/non-operational mode with the fluid in the housing, only the buoyant forces are acting on the rotor and the rotor floats up in the random position. In the stationary/non-operational mode with no fluid in the housing, the rotor is resting on the interior of the housing under gravitational forces.

Levitation of the rotor, as indicated, is achieved by a combination of hydrodynamic and buoyant forces. Briefly, the buoyant component is achieved as a result of careful selection of the rotor density, with the preferred relative density being between about 0.1 and 0.9 of the relative density of the fluid being pumped. In a dynamic and operational mode, the buoyant forces merely become a component of lesser or secondary importance to the more significant and more highly effective hydrodynamic force.

The hydrodynamic force component is achieved as a result of the motion of the fluid as it is being moved through the pumping chamber. As the velocity of the fluid increases, the hydrodynamic forces increase substantially, and with the proper selection of rotor density, the hydrodynamic forces which are created during normal operation result in achieving a precise, steady and controllably repeatable centering of the rotor within the pumping chamber.

The pump structure of the present invention has particular application for transferring fragile and/or aggressive liquids, in particular, for transferring human blood. Since certain components in blood are extremely fragile and are damaged upon exposure to external forces, conventional pumps are simply unsuited for the application. Additionally, conventional seals and/or bearings typically found within conventional pump structures pose substantial and significant threats to cell damage. A further feature of the pump of the present invention rendering the pump well suited for transfer of blood is its essentially friction-free operation. Any frictional force creates the risk of generation of thermal energy, and thus may contribute to heat build-up. Since blood is extremely sensitive to temperature change, particularly any increase in temperature above conventional body temperature, reduction and/or virtual elimination of friction provides significant and substantial advantages.

Since the structure of the present invention does not require bearings, energy consumption is reduced through the elimination of energy losses otherwise occurring in the bearings, including energy lost in contact bearings as well as electrical losses in magnetic bearings. The driving forces for the impeller are located generally adjacent the plane of the center of gravity or center of mass of the impeller, or more particularly at least closely adjacent thereto. This feature results in the creation of a gyroscopic effect of a free-body gyroscope, and the configuration of the present invention is such as to stabilize the impeller when the axis of the housing is rotated relative to the spin axis of the rotor. In other words, the spin axis of the rotor may be altered because of a change-of-position of the housing, and thus the spin axis may not always be about the vertical axis, but can be about the horizontal axis as well. In the present arrangement, particularly as illustrated in FIG. 2, it will be noted that the magnetic drive components are offset from the transverse axis of the rotor. In this configuration, it has been found that the center of gravity or center of mass of the rotor is generally displaced from the geometric center in a direction toward the mounting point of the drive.

In addition to blood pump applications, the device of the present invention finds utility in connection with other fluids as well. Certainly non-delicate fluids may be appropriately treated and/or moved with pump devices of the present invention including the aggressive fluids as discussed hereinabove.

The elimination of shafts, bearings and seals substantially reduces the manufacturing cost of the pump of the present invention. Also, the pump of the present invention has a mechanical lifetime which is virtually unlimited under normal conditions. The device of the present invention finds utility for a variety of fluids when economy, longevity, and uninterrupted service are factors in selection and/or application.

In accordance with the present invention, only one inlet to the housing is provided, and correspondingly only one line of plumbing to the pump is required. Offsetting the plane of the drive means from the outlet/medial plane of the housing further makes the pump design, operation, and maintenance more convenient and allows one to use a conventional drive means, especially in the permanent magnet-to-permanent magnet configuration.

SUMMARY OF THE INVENTION

Therefore, it is a primary object of the present invention to provide an improved pump for transferring fragile liquids such as human blood, and wherein the pump is bearing and seal-free, with the rotor being dynamically balanced by a combination of hydrodynamic and buoyant forces, and having an internal bore formed therewithin to transfer incoming fluid from one polar end of the rotor to the other.

It is yet a further object of the present invention to provide an improved pump for application with human blood which is capable of creating a uniform and consistent flow of such liquids without damaging or otherwise adversely affecting the quality of the material being pumped.

It is yet a further object of the present invention to provide a pump structure utilizing a pumping chamber housing a rotor wherein rotation of the rotor is achieved by an electromagnetic drive system operating in conjunction with an array of permanent magnets disposed on the rotor in a brushless configuration.

Other and further objects of the present invention will become apparent to those skilled in the art upon a study of the following specification, appended claims, and accompanying drawings.

IN THE DRAWINGS

FIG. 1 is a perspective view of a pump assembly prepared in accordance with the present invention;

FIG. 2 is a vertical sectional view taken through the axis of the rotor, and illustrating the flow patterns created by the pump when in actual operation;

FIGS. 3 and 4 are horizontal sectional views of the pump structure illustrated in FIG. 2, and taken along the lines 3—3 and 4—4 respectively of FIG. 2;

FIG. 5 is a fragmentary view on an enlarged scale and illustrating the magnitude of the clearance between the exterior of the rotor and the interior of the housing; and FIG. 6 is a schematic diagram illustrating a typical system in which the device of the present invention may function.

DESCRIPTION OF THE PREFERRED EMBODIMENT

In accordance with the preferred embodiment of the present invention and with particular attention being directed to FIGS. 1, 2 and 3 of the drawings, the pump generally designated 10 comprises a housing 11, the interior of which defines pumping chamber shown generally at 12. In other words, the inner periphery 13 of housing 11 is the outer periphery of the chamber 12. As is clear from the views of FIGS. 2, 3, and 4, housing 11 and chamber 12 share a central axis which extends along axis 14 as set forth in FIG. 2. Housing 11, and accordingly chamber 12, is provided with a primary inlet port as at 16, along with outlet ports as at 18 and 19. Inlet port 16 defines the inlet to the chamber, while outlet ports 18 and 19 collectively define the outlets. The external inlet port 16 is arranged coaxially with the chamber, that is, along axis 14, with the external inlet port being arranged in oppositely disposed relationship to secondary or internal inlet 17 adjacent apex 43 of deflector tip. Outlet ports 18 and 19 are arranged medially of the primary and secondary inlet ports, and are, as indicated, disposed generally transversely of axis 14.

With continued attention being directed to FIGS. 2 and 3 of the drawings, rotor 20 is disposed within chamber 12 and has a core component 21 with a symmetrical dual conical configuration. This configuration provides dual cones of arcuate configuration converging toward opposed polar regions such as 21 and 22, with the rotor being provided with an axis of rotation which extends between the polar regions 21 and 22, and generally along with and coincidental with axis 14. The base of each of the two cones forming the dual cone configuration are coupled together and form a common center plane as at 23. The rotor core 21 is also provided with a pair of conically configured shrouds, such as at 24, 25, 26 and 27. Shrouds 24, 25 and 26 are each generally conical in configuration with the cones being formed as the surface of revolution of an arcuate segment, the arcuate segment having a radius which substantially matches that of the dual cones. Additionally, shroud 27 has an inner arcuate segment as at 27A along with an outer segment as at 27B. Segments 27A and 27B are joined together at their ends so as to form an enclosed surface of revolution defined generally by arcuate segments 27A and 27B, with the resultant being a member having a modified toroidal configuration.

The individual shrouds are coupled to core component 21 by posts or spoked discs 28—28. Discs 28—28 provide a link between the outer surface 29 of core component 21, and thus provide the mechanical stability and rigidity for the overall assembly. The configuration of the core component 21 together with shrouds 24, 25, 26 and 27 define annular flow channels as at 31, 32, and 33 on the upper portion of the assembly along with similar annularly configured channels 34, 35, and 36 adjacent the lower portion of the assembly. Within the confines of modified toroidal member 27 are a series of permanent magnets such as magnets 37—37. These magnets are arranged at radially spaced locations generally medially along the axis of rotation of rotor 20, with the permanent magnets being provided at equally radially and arcuately spaced locations. Electromagnetic drive means are provided as at 38—38, with the electromagnetic drive means being, in turn, coupled to a source of electrical energy and arranged to deliver rotational driving energy to the rotor through the permanent magnets 37—37. The drive arrangement is, of course, commonly referred to as a brushless motor configuration and brushless motor drives are, of course, well known in the art. The rate of rotation of rotor 20 is conveniently controlled by means of the frequency of the field applied to electromagnetic members 38—38, with the rate of rotation being controlled by the frequency of the applied electromagnetic field, or by selective energization of the electromagnetic means 38—38. Such drives are, of course, commonly utilized and well known in the art.

Rotor 20 is defined by outer surface or wall 29, with the material of construction being either similar or identical to that employed in housing 11. A suitable biocompatible material such as polycarbonate, acrylic, or copolymers of polystyrene may be employed, or alternatively a coating may be applied to a suitable substrate in order to enhance the biocompatibility of the structure. In those instances where the device is not being employed for implantation, then, of course, other materials may be employed, provided that the blood-contacting surfaces be formed and/or coated with a non-thrombogenic material. If the rotor material has a lower density than a pumped fluid, the voids and/or cavities formed in the core and shroud may be eliminated.

Rotor 20 is provided with a tubular core 40 which defines an axial bore generally designated 41. Bore 41 accepts fluid from inlet 16 and transmits the fluid directly to secondary inlet zone or chamber 42, for ultimate transfer and flow through annular channels 34, 35 and 36. As indicated, each of these channels leads to outlet 18, thereby providing continuity of flow. An apex point is provided as at 43 in order to provide for smooth flow, preferably laminar flow, through the pump assembly.

In addition, a hollow core or void area is provided within rotor core 21, with this chamber being shown generally at 45. This chamber area provides a volume of a size or magnitude which in turn defines a means for controlling the relative density of the rotor body. Additional buoyancy is provided by the modified toroidal configuration of member 27, thereby providing an overall relative density for the rotor assembly. Preferably, the relative density is selected by the ratio of the relative density of the rotor or rotor assembly to that of the fluid being pumped, and in most applications, the relative density of the rotor to the fluid being pumped is between about 0.3 and 0.6, with it being understood that relative densities of between about 0.1 and 0.9 may be found useful. Also, the dual conical configuration of the core component 21 of rotor 20 together with shrouds provides the finished structure with an axial length along the axis of rotation as being generally equal to the axial length of the pumping chamber between the primary inlet port 16 and secondary inlet port area 42. The transverse diameter of the rotor 20 and its shrouds is defined along a medial plane, as along medial line 23 and with the configuration of the dual converging cones providing a clearance between the surface of the rotor and the inner surface of the pumping chamber as illustrated in greater detail in FIG. 5. Generally speaking, the clearance as indicated at A—A and B—B is such that the clearance remains constant from the primary and secondary inlet ports to the outlet ports. The combined area of the individual flow channels is such that the rate of motion for the fluid being pumped as it moves along its transitional and rotational motions and/or vectors is substantially constant. With these considerations in mind, the clearance between the inner surface of the pumping chamber and the periphery of the rotor preferably ranges from between about 1 millimeter up to about 7 millimeters, with a narrower range of between about 1 millimeter and 3 millimeters being generally preferred for blood. Generally, a clearance of about 1.5 millimeters is preferred.

With respect to the areas of the inlet and outlet ports, it is generally preferred that the combined area of the primary inlet port 16 is generally equal to the combined areas of the outlet ports 18 and 19, thereby providing more consistency in flow and pressures, and also providing for an appropriate hydrodynamic balancing of the rotor 20 within the chamber 12.

As has been indicated, the drive means for the electromagnetic drive elements 38—38 is preferably in the form of conductor windings, and for purposes of achieving appropriate hydrodynamic balance, the windings are carefully controlled and selectively made so as to preserve the hydrodynamic balance of the rotating rotor while eliminating the need for any form of bearing.

As has been indicated, the moment of inertia of the impeller is effectively minimized by virtue of the positioning of the mass of the impeller closer to the center of gravity or center of mass. This may be obtained by moving the mass of the impeller needed for structural integrity closer to the center, and generally as closely as possible to the rotational axis. The moment of inertia may be controllably adjusted in connection with the structure of the present invention by arranging and mounting the permanent magnets within a circular or annular zone which is at the maximum radius of the rotor inner impeller, as required, while increasing the strength of the structure along its axis of rotation. As is indicated in FIG. 2, for example, permanent magnets 37—37 are positioned within the confines of modified toroidal member 27, thereby effectively isolating the permanent magnets from contact with the fluid being pumped.

With respect to the fluid being pumped, it should be noted that the human blood has a viscosity of about 4 centipoises at 25° C., and this viscosity is sufficient to provide for sufficient friction between relatively smooth rotor and shroud surfaces and blood so as to achieve a sufficient rotational component of motion for hydrodynamic balancing. As the rotational velocity of the fluid being pumped increases, its hydrodynamic balance effect will, of course, increase correspondingly and proportionately. With a rotational velocity of approximately 1000 rpm, the hydrodynamic balancing effect substantially overwhelms the buoyant effect afforded by the relative density of the rotor within the chamber.

For start-up purposes, saline is normally preferred as the functional material, with the saline being employed for a period of time until the desired rotational velocity is achieved, and thereafter blood may be introduced as the working solution being pumped and/or transferred.

While the rotor structure illustrated is described as being relatively smooth, vanes may be employed on the structure with the vanes forming arcuately spaced passages within the rotor. In other words, vanes, if employed, may be formed as individual arcuately spaced paddles to form spaced-apart fluid passages and/or channels.

The inlet and outlet diameters are preferably 7 millimeters and the relative density is preferably between 0.1 to 0.9, with a relative density of 0.5 being preferred.

For most operational purposes, an inlet pressure ranging from between about 5 millimeters of Hg (mercury) up to about 40 millimeters Hg (mercury) is considered normal and appropriate for fluid dynamics dealing with human blood. Outlet pressures of between about 40 millimeters Hg (mercury) up to about 150 or 200 millimeters Hg (mercury) may be employed. When the device of the present invention is functioning as an implantable unit, the outlet pressure will, of course, depend upon the patient's activity and circulatory requirements being indicated.

Attention is now directed to FIG. 6 of the drawings wherein a system is illustrated for utilization of the pump device of the present invention as a patient-assist unit. In the drawing of FIG. 6, the pump 50 may be employed as a device with the outlets coupled to the aorta. In an alternative construction, the outlet may be coupled to the pulmonary artery. As indicated, the device of the present invention has application as a transfer pump as well, and may be employed, therefore, in surgical procedures which involve temporarily removing and/or temporarily disabling the heart function.

The pump 50 is coupled in a system which functions as a ventricular or heart-assist device. Pump 50 is powered by power supply 51 and sensors, including pickup ratio sensor 52 and ratio control 53 are employed. The patient pressure level monitor 55 provides an input to ratio control 53 with the level monitor 55 receiving information, including patient pressure level input as at 54 and pressure level signal 56. These systems are known in the art and may be employed effectively in connection with the device of the present invention.

While double cones have been discussed, it is possible that multiple cones may be employed in lieu of vanes, wherein the rotor is provided with surfaces of revolution disposed axially outwardly of the rotor, and with the surfaces of revolution being arranged coaxially with the axis of rotation of the rotor.

While the term "double conical configuration" has been employed throughout, it will be understood that other surfaces of revolution may be employed, such as those surfaces of revolution generated by a curved line such as parabola, hyperbola, or a straight line so as to form a cone. Thus, the term "cone" is understood to be broadly defined herein.

It will be appreciated, of course, that various modifications may be made in the preferred embodiment illustrated above, and these modifications may be made without actually Departing from the spirit and scope of the present invention.

What is claimed is:

1. A pump for transferring fluids and comprising a pumping chamber with an inner periphery, an outer periphery and a central axis, primary and secondary fluid inlet ports arranged in oppositely disposed relationship on said chamber and coaxially with said pumping chamber, an outlet port means arranged transversely and generally medially of said primary and secondary inlet ports, a rotor disposed within said pumping chamber and having a core with a dual conical configuration converging toward opposed polar regions and having an axis of rotation extending between said polar regions and arranged coaxially with the axis of said pumping chamber during operational rotation of said rotor, magnetic driven means arranged on said rotor at radially spaced locations generally from said axis of rotation, electromagnetic drive means coupled to a source of energy and arranged to deliver rotational driving energy to said rotor through said magnetic driven means; said rotor comprising:

(a) a core with at least one shroud coupled to the outer surface of said core having a semi-conical configuration with a core axial length and with the core axial length defining the axial length of said pumping chamber, and with said pumping chamber being disposed between said primary and secondary inlet ports; and with the diameter of said core and shroud transverse to said axis of rotation defining a medial plane and being selected to provide a clearance between the outer surface of said shroud and the inner surface of said pumping chamber and with the magnitude of the clearance between the said inner surface of said pumping chamber and the outer periphery of said shroud from said primary and secondary inlet ports to said outlet port being approximately constant.

2. The pump as in claim 1 wherein the clearance between the inner surface of said pumping chamber and the outer periphery of said shroud is from between about 1 millimeter and 7 millimeters.

3. The pump of claim 1 having plural outlet ports, with the sum total of the cross-sectional area of said outlet ports being substantially equal to the cross-sectional area of said inlet ports.

4. The pump of claim 3 where the said plurality of outlet ports are generally equally arcuately spaced, one from another.

5. The pump of claim 2 wherein said clearance between the inner surface of said pumping chamber and the outer surface of said shroud is adequate to provide a flow channel for blood, and is such that the velocity of fluid being pumped remains substantially constant between said primary and secondary inlet ports and said outlet ports relative to the surface of said housing.

6. The pump of claim 1 wherein the rate of rotation of said rotor is controllably variable.

7. The pump of claim 1 being particularly characterized in that means are provided for sensing the rotational velocity of said rotor.

8. The pump of claim 1 being particularly characterized in that the driving forces for said rotor are coupled to said magnetic driven means disposed in spaced relationship to the center of mass of the rotor.

9. The pump of claim 1 being particularly characterized in that the fluid flows from inlets adjacent the polar tips of the cones to outlets adjacent the medial plane.

10. The pump as defined in claim 1 wherein the drive means includes permanent magnets arranged within the rotor along radial points adjacent the outer circumference of the rotor.

11. The pump as defined in claim 1 wherein the drive means includes permanent magnets disposed in a circular array, and wherein the outer perimeter of the magnets forming the array are spaced from the mid-point thereof, and with the structural mass of the rotor being disposed adjacent the rotational axis, thereby reducing the moment of inertia of said rotor.

12. A pump for transferring fluids especially liquids and comprising a pumping chamber with an inner periphery, an outer periphery and a central axis, inlet port means arranged in polar relationship to said pumping chamber and coaxially with said pumping chamber during operational rotation of said rotor, an outlet port means arranged transversely and generally medially of said pair of inlet ports, a rotor disposed within said pumping chamber and having a dual conical configuration converging toward opposed polar regions and having an axis of rotation extending between said polar regions and arranged coaxially with the axis of said pumping chamber, magnetic driven means arranged on said rotor at radially spaced locations generally medially along said axis of rotation, electromagnetic drive means coupled to a source of energy and arranged to deliver rotational driving energy to said rotor through said magnetic driven means; said rotor comprising:

(a) a core with at least one shroud coupled to the outer surface of said core having a semi-conical configuration with a core axial length and with the core axial length defining the axial length of said pumping chamber, and with said pumping chamber being disposed between said primary and secondary inlet ports; and with the diameter of said core and shroud transverse to said axis of rotation defining a medial plane and being selected to provide a clearance between the outer surface of said shroud and the inner surface of said pumping chamber and with the magnitude of the clearance between the said inner surface of said pumping chamber and the outer periphery of said shroud from said primary and secondary inlet ports to said outlet port being approximately constant; and (b) the arrangement being such that the sole support for the rotor are the hydrodynamic forces created in the fluid being pumped, wherein the housing structure of the pump is free of rotor supporting members and bearings.

* * * * *